(12) United States Patent
McDermott et al.

(10) Patent No.: US 7,867,779 B2
(45) Date of Patent: Jan. 11, 2011

(54) SYSTEM AND METHOD COMPRISING SAME FOR MEASUREMENT AND/OR ANALYSIS OF PARTICLES IN GAS STREAM

(75) Inventors: Wayne Thomas McDermott, Fogelsville, PA (US); Richard Carl Ockovic, Northampton, PA (US); Dean Van-John Roth, Center Valley, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1008 days.

(21) Appl. No.: 11/340,641

(22) Filed: Jan. 27, 2006

(65) Prior Publication Data

US 2006/0172428 A1    Aug. 3, 2006

Related U.S. Application Data

(60) Provisional application No. 60/649,490, filed on Feb. 3, 2005, provisional application No. 60/723,619, filed on Oct. 4, 2005.

(51) Int. Cl.
*G01N 1/22* (2006.01)
(52) U.S. Cl. .................. 436/181; 436/148; 436/174; 436/175; 436/177; 436/178; 422/83; 422/88; 422/93
(58) Field of Classification Search ................ 436/148, 436/164, 167, 174, 175, 177, 178, 181, 52; 422/81, 82.05, 83, 88, 93
See application file for complete search history.

(56) References Cited

U.S. PATENT DOCUMENTS

| | | | |
|---|---|---|---|
| 4,014,216 A | 3/1977 | Thornton et al. |
| 4,250,053 A | 2/1981 | Smith |
| 4,371,605 A | 2/1983 | Renner |
| 4,442,197 A | 4/1984 | Crivello et al. |
| 4,491,628 A | 1/1985 | Ito et al. |
| 4,603,101 A | 7/1986 | Crivello |
| 4,624,912 A | 11/1986 | Zweifel et al. |
| 4,878,510 A | 11/1989 | Kasper et al. |
| 4,883,507 A | 11/1989 | Rey et al. |
| 4,962,673 A | 10/1990 | Wang et al. |
| 4,964,278 A | 10/1990 | Wen et al. |

(Continued)

FOREIGN PATENT DOCUMENTS

CN    1118438 A    3/1996

(Continued)

OTHER PUBLICATIONS

W. Zorn; "Particle Counting of Liquid Systems Using a Scanning Electron Microscope"; Particle in Gases and Liquids 1, Detection, Characterization, and Control; 1989; Plenum Press, New York.

(Continued)

*Primary Examiner*—Maureen M Wallenhorst
(74) *Attorney, Agent, or Firm*—Rosaleen P. Morris-Oskanian

(57) ABSTRACT

A system and method for measuring and analyzing particles within a gas feed stream. In one aspect, the system includes a particle counter and a particle capture filter that are arranged in parallel. In another aspect, the system includes a purifying device to remove trace molecular impurities from a gas feed stream to reduce the presence of impurities.

22 Claims, 5 Drawing Sheets

U.S. PATENT DOCUMENTS

| | | | |
|---|---|---|---|
| 5,209,102 A | 5/1993 | Wang et al. | |
| 5,537,879 A | 7/1996 | Malczewski et al. | |
| 5,591,273 A | 1/1997 | Tsukamoto et al. | |
| 5,618,996 A | 4/1997 | Wang et al. | |
| 5,665,902 A | 9/1997 | Wang et al. | |
| 5,814,741 A | 9/1998 | Wang et al. | |
| 5,872,622 A | 2/1999 | Schildmeyer et al. | |
| 5,880,355 A | 3/1999 | Park et al. | |
| 5,992,216 A | 11/1999 | Wang et al. | |
| 5,996,420 A | 12/1999 | Lee | |
| 6,054,206 A | 4/2000 | Mountsier | |
| 6,054,379 A | 4/2000 | Yau et al. | |
| 6,159,871 A | 12/2000 | Loboda et al. | |
| 6,171,945 B1 | 1/2001 | Mandal et al. | |
| 6,182,519 B1 | 2/2001 | Kimura et al. | |
| 6,248,217 B1 | 6/2001 | Biswas et al. | |
| 6,258,407 B1 | 7/2001 | Lee et al. | |
| 6,329,118 B1 | 12/2001 | Hussein et al. | |
| 6,365,529 B1 | 4/2002 | Hussein et al. | |
| 6,368,400 B1 | 4/2002 | Baldwin et al. | |
| 6,437,443 B1 | 8/2002 | Grill et al. | |
| 6,441,491 B1 | 8/2002 | Grill et al. | |
| 6,448,185 B1 | 9/2002 | Andideh et al. | |
| 6,469,780 B1 * | 10/2002 | McDermott et al. | 356/37 |
| 6,506,692 B2 | 1/2003 | Andideh | |
| 6,515,073 B2 | 2/2003 | Sakamoto et al. | |
| 6,573,175 B1 | 6/2003 | Yin et al. | |
| 6,583,048 B1 | 6/2003 | Vincent et al. | |
| 6,583,104 B1 | 6/2003 | Christensen et al. | |
| 6,605,362 B2 | 8/2003 | Baldwin et al. | |
| 6,627,546 B2 | 9/2003 | Kneer | |
| 6,632,707 B1 | 10/2003 | Wang et al. | |
| 6,677,286 B1 | 1/2004 | Rovito et al. | |
| 6,680,262 B2 | 1/2004 | Andideh et al. | |
| 6,726,770 B2 | 4/2004 | Eichinger | |
| 6,743,712 B2 | 6/2004 | Park et al. | |
| 6,774,032 B1 | 8/2004 | Park | |
| 6,800,548 B2 | 10/2004 | Andideh | |
| 6,803,307 B1 | 10/2004 | Chu | |
| 6,818,829 B1 | 11/2004 | McMillan et al. | |
| 6,828,289 B2 | 12/2004 | Peters et al. | |
| 6,846,515 B2 | 1/2005 | Vrtis et al. | |
| 6,849,561 B1 | 2/2005 | Goundar | |
| 6,858,528 B2 | 2/2005 | Meagley et al. | |
| 6,872,666 B2 | 3/2005 | Morrow | |
| 6,876,017 B2 | 4/2005 | Goodner | |
| 6,905,613 B2 | 6/2005 | Gutierrez et al. | |
| 6,956,097 B2 | 10/2005 | Kennedy et al. | |
| 6,965,097 B2 | 11/2005 | Lee | |
| 6,969,425 B2 | 11/2005 | Cabuz et al. | |
| 6,969,753 B2 | 11/2005 | Baldwin et al. | |
| 2001/0055725 A1 | 12/2001 | Hussein et al. | |
| 2002/0083780 A1 * | 7/2002 | Lutz et al. | 73/863.01 |
| 2002/0180051 A1 | 12/2002 | Grill et al. | |
| 2003/0064580 A1 | 4/2003 | Ott et al. | |
| 2003/0130146 A1 | 7/2003 | Egbe et al. | |
| 2003/0148910 A1 | 8/2003 | Peters et al. | |
| 2003/0197852 A1 | 10/2003 | Johnson et al. | |
| 2003/0224156 A1 | 12/2003 | Kirner et al. | |
| 2004/0009662 A1 | 1/2004 | Park et al. | |
| 2004/0016904 A1 | 1/2004 | Baum et al. | |
| 2004/0048960 A1 | 3/2004 | Peterson et al. | |
| 2004/0063042 A1 | 4/2004 | Egbe | |
| 2004/0077175 A1 | 4/2004 | Hsieh et al. | |
| 2004/0099954 A1 | 5/2004 | Chen et al. | |
| 2004/0152608 A1 | 8/2004 | Hsu | |
| 2004/0266637 A1 | 12/2004 | Rovito et al. | |
| 2005/0017364 A1 | 1/2005 | Iba | |
| 2005/0029229 A1 | 2/2005 | Chae et al. | |
| 2005/0029627 A1 | 2/2005 | Dennison | |
| 2005/0070116 A1 | 3/2005 | Fu et al. | |
| 2005/0095841 A1 | 5/2005 | Chen et al. | |
| 2005/0106886 A1 | 5/2005 | Goodner et al. | |
| 2005/0124149 A1 | 6/2005 | Kim et al. | |
| 2005/0124152 A1 | 6/2005 | Meagley et al. | |
| 2005/0136687 A1 | 6/2005 | Lu et al. | |
| 2005/0145890 A1 | 7/2005 | Goodner | |
| 2005/0176602 A1 | 8/2005 | Hsu | |
| 2005/0176603 A1 | 8/2005 | Hsu | |
| 2005/0221218 A1 | 10/2005 | Clark et al. | |
| 2005/0239281 A1 | 10/2005 | Goodner et al. | |
| 2005/0239673 A1 | 10/2005 | Hsu | |
| 2005/0245075 A1 | 11/2005 | Arita et al. | |
| 2005/0260845 A1 | 11/2005 | Ali | |
| 2006/0009025 A1 | 1/2006 | Kanamura | |
| 2006/0009031 A1 | 1/2006 | Kloster et al. | |

FOREIGN PATENT DOCUMENTS

| | | |
|---|---|---|
| CN | 1531646 A | 12/2008 |
| EP | 0 242 564 A2 | 10/1987 |
| EP | 242564 | 10/2003 |
| JP | 2-98652 A | 4/1990 |
| JP | 2-298302 A | 12/1990 |
| JP | 4-303738 A | 10/1992 |
| JP | 04-303738 A | 10/1992 |
| JP | 5-034260 A | 2/1993 |
| JP | 05-034260 A | 2/1993 |
| JP | 8-101116 A | 4/1996 |
| JP | 08-101116 A | 4/1996 |
| JP | 8-327509 A | 12/1996 |
| JP | 08-327509 A | 12/1996 |
| JP | 10-253509 A | 9/1998 |
| JP | 2000180342 | 6/2000 |
| WO | WO 99/41423 | 8/1999 |
| WO | 02/23155 A2 | 3/2002 |
| WO | 2004/046517 A2 | 6/2004 |
| WO | 2004/097400 A1 | 11/2004 |
| WO | WO 2004/097400 A | 11/2004 |

OTHER PUBLICATIONS

K. Kondo, K. Ichijo, K. Shinohara, T. Hoshina, K. Tsubouchi, and K. Masu; "In-Situ Counting of Process-Induced Particles"; Japanese Journal of Applied Physics; Mar. 1992; pp. 918-920; vol. 31, Pt. 1, No. 3; Japan.

W. Plante, K. Vakhshoori, R. Binder; "Formation and Control of Particles in Silane Gas Delivery Systems"; Journal of Aerosol Science; 1993; pp. S41-S42, vol. 24, Suppl. 1, Pergamon Press Ltd.

W. Plante, K. Vakhshoori, R. Binder; "Controlling Particles in Silane Gas Delivery Systems"; Microcontamination Conference Proceedings; 1993; pp. 443-452.

S. Laly, K. Nakagawa, T. Kimijima, S. Taguchi, T. Ikeda, and S. Hasaka; "Determination of Particle-Bound Metallic Impurities in Semiconductor Grade Gases. 1. Silane"; Analytical Chemistry; Dec. 15, 1996; pp. 4312-4315; vol. 68, No. 24; American Chemical Society.

"Mobile Multigas Monitoring System Features Particle Analysis Instrument"; CleanRooms; Apr. 1998.

W. McDermott and A. Budihardjo; "Particle Measurement in Semiconductor Processing Gases: An Overview"; presented at the Semiconductor Equipment and Materials International IC Seminar, Singapore, May 1999.

W. McDermott; "Particle Measurement in Semiconductor Process Gases"; Solid State Technology; Aug. 1999; pp. 65-70; vol. 42 (8).

B. Gotlinski, J. O'Sullivan, M. Horikoshi, and S. Babasaki; "Eliminating Siloxane Impurities from Silane Process Gas Using Next-Generation Purification"; Micro Magazine; Jul. 2000; Cannon Communications LLC.

Y. Mamane, R. Willis, and T. Conner; "Evaluation of Computer-Controlled Scanning Electron Microscopy Applied to an Ambient Urban Aerosol Sample"; Aerosol Science and Technology; 2001; pp. 97-107; vol. 34; Taylor and Francis.

W. McDermott; "Capture and Analysis of Particulate Contamination in Dense Phase $CO_2$"; Standards Workshop on Contamination, Measurement in Liquid $CO_2$; SEMICON West; Jul. 2004.

European Search Report 06002182.1-2204, dated Aug. 5, 2006.

* cited by examiner

SYSTEM AND METHOD COMPRISING SAME FOR MEASUREMENT AND/OR ANALYSIS OF PARTICLES IN GAS STREAM

CROSS-REFERENCE TO RELATED APPLICATIONS

This application claims the benefit of priority under 35 U.S.C. §119(e) to earlier filed U.S. patent application Ser. No. 60/649,490 filed on Feb. 3, 2005, and to earlier filed U.S. patent application Ser. No. 60/723,619 filed on Oct. 4, 2005, the disclosures of which are incorporated herein by reference.

BACKGROUND OF THE INVENTION

The present invention relates to a system and method for sampling a gas feed stream to determine the presence and characteristics of particulate contaminants in the gas stream. In particular, the present invention relates to a system comprising a particle counter and a particle capture filter, wherein the particle capture filter is advantageously arranged in parallel with the particle counter.

Many users of specialty gases, such as semiconductor device manufacturers, require low suspended particle content in the gases. For example, particulate contamination in fabricating materials causes low yield in the device fabrication process, and reliability problems in finished semiconductor devices. Therefore, strict cleanliness requirements are routinely imposed upon gases such as, but not limited to, Ar, He, $N_2$, Xe, Kr, Ne, $SiH_4$, $SiH_2Cl_2$, $NH_3$, $BCl_3$, $CO_2$, CO, $N_2O$, $O_2$, $H_2$, $SiHCl_3$, $PH_3$, $AsH_3$, $BF_3$, $B_2H_6$, $Si_2H_6$, $SiCl_4$, and many others.

Particulate levels in gas feed streams may vary between being a relatively uniform and steady stream or, for example, as the tool interface is approached, variable over a period of time. Variability in the gas feed stream can take the form of burst states (spikes), time-varying drift (upward or downward), and/or step changes (upward or downward). In dynamic systems, such as, for example, flowing transfill systems and tool feed lines, the gas feed stream is usually well mixed and particles are uniformly distributed. However, in static systems, such as, for example, gas cylinders or other supply vessels, particulate levels can vary spatially by orders of magnitude. This particle variation may be attributable to such effects as gravitational settling and diffusion to internal surfaces. Such effects produce non-uniform particulate distributions, including stratification, in the supply vessel.

Cylinder and bulk gases are frequently reduced in pressure with an automatic regulator before entering the gas feed stream. This reduction in pressure of the gas feed stream may produce, for example, increased particulate levels through regulator "shedding", impurities nucleation, and condensational droplet formation. In certain situations, suspended non-volatile residue formation may occur.

In addition to the above issues, if the gas feed stream comprises a reactive gas such as, for example, silane, the reactive gas may combine with atmospheric contaminants to form suspended solid material (particles). Reaction of silane with oxygen or oxidizing agents produces silica ($SiO_2$) dust in the form of particles. Any trace moisture or oxygen in silane storage/transfer systems can be expected to produce copious amounts of fine particulate silica. These solid reaction products can produce a significant inaccuracy in any measurement of the suspended particle content. Such particulate generation persists until the oxygen or oxidizing agents in the system are consumed and the source of the agents is eliminated. Because of these and other issues, careful attention to the detection and removal of atmospheric contaminants may be necessary for gas feed streams comprising reactive gases.

Particle formation in a gas feed typically often results from the presence of molecular impurities. Many semiconductor processing gases are supplied in pressurized vessels. It is common for such high purity gases to contain trace molecular impurities, such as, for example, hydrocarbons in nitrogen, siloxanes in silane, and other such impurities depending upon the composition of the high purity gas. These impurities may result from the processes used to produce, transfer and store the gases in pressurized containers. The internal pressure and temperature of the gas storage vessel are frequently well above the critical point pressure and critical point temperature of the gas. For example, the critical points of $N_2$ (492 psia, −232° F.) and $SiH_4$ (703 psia, 26° F.) are typically exceeded in gas storage vessels as delivered to users. It is well known that supercritical fluids have a high solvent power for materials, such as higher molecular weight hydrocarbons, which may exist as surface contaminants in gas transfer, storage and delivery systems. These dissolved impurities may add to the molecular impurities typically present in the gas.

In order to control process variables that contribute to particulate contamination in gases and to ensure the quality of the gas, accurate particle measurement from pressurized gas sources is performed. It is desirable to measure the suspended particle concentration in the pressurized gas. However, due to the pressure limitations of available instrumentation, it may not be practical to measure the particle content at the full pressure of the storage vessel. Consequently, the gas sample is transferred through a pressure reducing device, such as, for example, an automatic pressure regulator, valve, flow restricting orifice, or the like, in order to reduce the gas pressure to a level compatible with the available instrumentation for particle measurement. This measurement may be conducted in-line or off-line relative to the gas feed stream.

It is well known in the art of particle measurement that gases having trace quantities of molecular impurities suffer an increase in particle content as the gas pressure is reduced. This degradation results from molecular clustering of trace impurities leading to formation of stable (i.e., persistent) suspended particles. These particles cannot be easily vaporized through heating. Further, in certain instances, the process of pressure reduction frequently produces sub-critical conditions in the gas. In this regard, the sub-critical gas loses its high solvent power following pressure reduction. Any dissolved impurities therefore tend to form stable suspended particles in the sample gas stream. Particle formation during pressure reduction is known to produce particles levels of over $10^6$ per standard cubic foot of gas for particles larger than 0.02 micrometer. This level substantially exceeds the actual level of particles in the pressurized vessel. FIG. 1 provides an example of a typical gas feed stream 1 that is passed through a pressure reducing device such as valve 2 that is in fluid communication with gas feed stream 1. While gas feed stream initially contains low levels of gas-borne particles 3, after passing through valve 2, the amount of particles contained within gas feed stream 1 or "nucleated" particles 4 increases. These nucleated particles 4 within lower pressure gas stream 5 are carried to the downstream particle counter instrument (not shown). The actual particle concentration in the vessel cannot then be discerned from the measurement. The pressure reduction process therefore substantially degrades the accuracy of particle measurement.

Previous attempts to solve the problem include construction of pressure resistant particle counters. Such instruments eliminate the need for sample gas pressure reduction upstream of the instrument. These instruments, however, cannot provide information on composition and morphology of the measured particles.

Similarly, low pressure instruments may be placed in custom-built pressurized chambers (e.g., hyperbaric chambers) and operated near the source gas pressure. However, this is an expensive and difficult modification to the instrument design and therefore suffers from practical problems.

Pressurized filter devices may also be used to capture particles from the sample stream without prior pressure reduction. These captured particles can then be examined using various means, such as optical microscopy, scanning electron microscopy, digestion or dissolution in liquid media followed by compositional analysis of the liquid, etc. However, this test method cannot discriminate between particles originating in the gas supply source and those spurious particles formed in the sampling system.

The problematic molecular impurities in the pressurized gas may be removed prior to pressure reduction using various absorbents, adsorbents, catalytic purifiers and other devices well known in the art of gas purification. This method has been known to substantially reduce or eliminate particle formation during pressure reduction. Such purifiers, however, operate by passing the gas feed stream through a bed of granular or pelletized purifying medium. This bed would tend to also act as a filter to remove actual particles flowing from the pressurized vessel or may introduce new particles to the stream from the purifying medium. Therefore, the actual particle content in the pressurized vessel cannot be accurately determined downstream of a bed-type purifier.

Gas stream heating and heating of the pressure reducer device have been used in an attempt to prevent nucleation of impurities during pressure reduction. This method is usually not effective in preventing the formation of nucleated particles in the expanded gas stream.

Accordingly, there is a need in the art for an improved, reliable system for measuring and/or analyzing particles within a gas feed stream that effectively removes molecular impurities before such impurities contribute to false impurity measurements.

BRIEF SUMMARY OF THE INVENTION

In one aspect, the present invention provides a system for measuring and/or analyzing particles within a gas feed stream, the system comprising a particle counter and a particle capture filter, wherein the particle capture filter is arranged in parallel with the particle counter.

In another aspect, the present invention provides a system for measuring particle content within a lower pressure gas feed stream, the system comprising a purifying device to remove impurities within a gas feed stream and provide a purified gas feed stream, a pressure reducing device in fluid communication with the purifying device wherein the purified gas feed stream is passed through the pressure reducing device to provide the lower pressure gas feed stream, a particle counter that measures the particle content within the lower pressure gas feed stream, and a particle capture filter, wherein the particle capture filter is arranged in parallel with the particle counter.

In yet another aspect, the present invention provides a method for measuring particle content within a lower pressure gas feed stream, the method comprising the step of passing a gas feed stream through a purifying device to provide a purified gas feed stream wherein the purifying device does not substantially remove the particles contained within the purified gas feed stream, wherein the gas feed stream is at a first pressure. The method also comprises the step of directing a portion of the purified gas feed stream to a pressure reducing device to reduce the pressure of the portion of purified gas feed stream to a pressure that is lower than the first pressure and measuring the particle content contained within the purified gas feed stream by passing the portion of purified gas feed stream that is at a pressure lower than the first pressure to a particle counter and by passing another portion of the purified gas feed stream to a particle capture filter. The particle capture filter is arranged in parallel with the particle counter.

BRIEF DESCRIPTION OF SEVERAL VIEWS OF THE DRAWINGS

The numerous advantages of the present invention may be better understood by those skilled in the art by reference to the accompanying non-scale figures in which like numerals represent like elements, and in which.

DETAILED DESCRIPTION OF THE INVENTION

Figure 1:
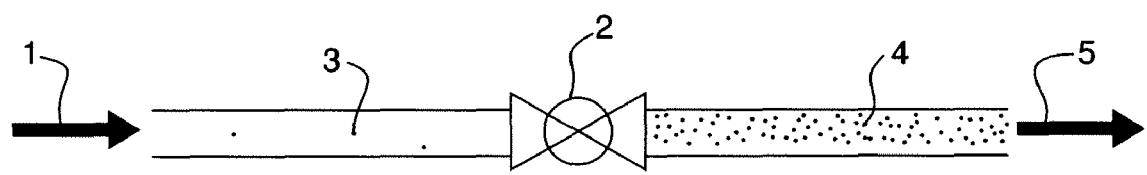
FIG. 1 is an illustration of a typical gas feed stream that is passed through a pressure reducing device.

A system and method that can be used for the measurement and/or analysis of particles within a gas feed stream is described herein. The system and method may be used to determine, for example, the number of particles or particle count; the concentration density of particles within the gas feed stream; the particle size distribution, particle morphology; and/or particle composition. The average size of the particle that can be measured within the gas feed stream may range from 0.02 microns ($\mu m$) to 10 $\mu m$, or from 0.05 $\mu m$ to 1 $\mu m$, or from 0.1 $\mu m$ to 1 $\mu m$. The average amount of particles that can be measured may range from 1/sq. ft. (sq. ft.) to 10,000,000 sq. ft., or from 1/sq. ft. to 10,000 sq. ft., or from 1/sq. ft. to 1,000 sq. ft.

The system and method can be used for a variety of gas and supercritical fluid feed streams including pyrophorics, flammables, oxidants, corrosives, and inert gases. Examples of gas feed streams that can be analyzed include electronic specialty gases ("ESGs") such as, but not limited to, inert gases (e.g., Ar, He, $N_2$, Xe, Kr, Ne, etc.), $SiH_4$, $CF_4$, $WF_6$, $SiH_2Cl_2$, $NH_3$, $NF_3$, $Cl_2$, $BCl_3$, $C_2F_6$, $CO_2$, $CO$, $F_2$, $N_2O$, $CHF_3$, $O_2$, $H_2$, $HBr$, $HCl$, $HF$, $CH_4$, $SiHCl_3$, $SF_6$, $PH_3$, $AsH_3$, $BF_3$, $B_2H_6$, $Si_2H_6$, $SiCl_4$, $SiF_4$, and many others. The term "gas" encompasses, vapors, supersaturated gases, and supercritical fluids. Examples of particular supercritical fluids are provided in pending U.S. Published Application 2004/0144399, which is incorporated herein by reference in its entirety. The system may be used, for example, to measure and/or analyze a variety of particulates which may include, for example, molecular clusters, liquid droplets, suspended solid particulates consisting of metallic, organic or other materials, and various other contaminating particles.

The system described herein measures and analyzes particles within a representative sample of a process gas stream by using a particle counter and a particle capture filter. The system does not add or remove a significant number of particles from the gas feed stream. Such interferences could change the measured particle concentration in the gas feed stream being sampled. In certain embodiments, electro-polished tubing and/or high cleanliness valves may be used to reduce sampling bias. Further, in these and other embodiments, the system minimizes transport losses of particles resulting from gravitational settling or diffusion to tube walls by reaction to molecular Brownian motion.

The system described herein may be used in conjunction with a continuous process feed stream or with side stream or sample stream extraction systems, described herein as "off-line sampling". The system described herein may also be used in conjunction with one of the gas sample extraction devices well known in the art, including so-called isokinetic sample probes, inserted into the feed gas line. In this connection, a separate stream to be sampled, which is referred to herein as the gas feed stream, is withdrawn from the process gas line, pressurized gas cylinder, or ISO module (i.e., an arrangement of cylindrical tubes in a single integrated unit suitable for bulk transport of gases). The off-line sample system may require venting or other form of emission control of the gas feed stream that is flowed through the particle counter or particle capture filter. In embodiments where the gas feed stream comprises a reactive gas, the off-line sample system may further include sub-systems to provide inert purging (i.e., purging the gas line with one or more inert gases), evacuation (i.e., evacuating the gas line using one or more vacuum pumps), and/or emission control. In other embodiments, such as when the gas feed stream comprises easily condensable gases (i.e., gases that become liquids at a temperature at or above ambient), the system lines and/or system components contained therein may also be heat traced. In these embodiments, heat tracing may be used in combination with inert purging and/or pressure cycling (i.e., employing a pressure variation) prior to introduction of the gas feed stream into the line for initial system drying because the gas may react with trace residual moisture or oxidizers in the line.

Figure 2:
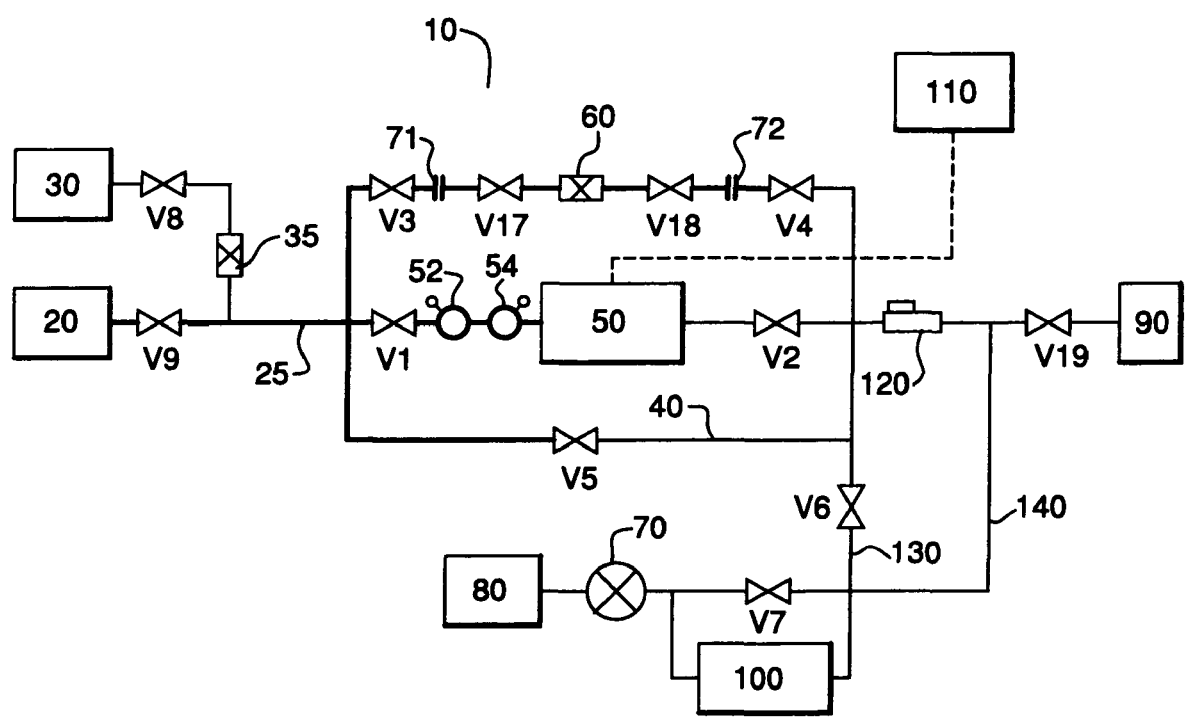
FIG. 2 is a schematic representation of a system in accordance with one embodiment of the present invention described herein as an off-line sample system.

FIG. 2 provides an example of one embodiment of an off-line sample system according to the present invention used to measure and analyze particles within a gas stream containing silane. In certain embodiments, such as that depicted in FIG. 2, system 10 is housed within a ventilated enclosure and is at ambient temperature. The gas feed stream 25 may be provided from supply source 20 such as a storage tank, pressurized gas cylinder, transfill line, gas distribution line, or other means (not shown). Supply source 20 may be large or small volume. At least a portion of the gas from supply source 20 is removed to provide a gas feed stream 25 which is fed through sampling system 10. Gas feed stream 25 is typically introduced into system 10 at a pressure ranging from 4 psia to 10,000 psig, or from 0 psig to 3,000 psig, or from 100 psig to 1,600 psig, depending upon, for example, the supply source volume, the identity of the gas feed stream 25, whether the gas contained therein is in a supercritical state, etc. System 10 further includes inert gas source 30 that is in fluid communication with system 10 and used for inert gas purging and other means. Inert gas purifier 35 is fluidly connected to inert gas source 30 to provide a purified inert gas for such purging/flushing operations.

In embodiments where gas feed stream 25 comprises silane, an inert gas purge followed by one or more evacuation cycles should be conducted prior to the introduction of the gas feed stream. Still referring to FIG. 2, an inert gas purge is conducted by closing valves V9 and V19 and opening valves V7 and V8. After the gas feed stream 25 has been analyzed, an inert gas purge may be run in a similar manner to remove any residual silane from the system. An evacuation cycle is conducted by closing valves V8, V9, and V19 and opening valve V7.

The embodiment depicted in FIG. 2 employs particle counter 50 and/or a particle capture filter 60 such as a membrane type filter to measure and detect the particles within the gas feed stream. Particle counter 50 can be connected to the gas feed source through a plurality of pressure regulators. Flow through the instrument is regulated by a flow control valve and a mass flow meter. In certain embodiments, the system operates at a pressure of near atmospheric pressure. In these embodiments, pressure reduction of the incoming gas feed stream 25 may be required between supply source 20 and particle counter 50. In the system shown in FIG. 2, the pressure reduction is performed in two steps using two pressure regulators, 52 and 54, arranged in series. Such multi-step pressure reduction minimizes particle shedding and gas condensation which tends to occur during the pressure reduction process. In other embodiments of the invention, a single step pressure reduction may be used. In other embodiments, gas feed stream 25 going to particle counter 50 may not need to be reduced because its pressure is sufficiently low.

In other preferred embodiments of the present invention, particle counter 50 is pressure resistant or enclosed in a pressure resistant containment vessel (not shown in FIG. 2). When the instrument or containment vessel can withstand the full pressure of the gas source 20, pressure reduction of the sample stream is not necessary. In this embodiment pressure regulators 52 and 54 are not required to obtain accurate measurement of the suspended particle content of the gas stream.

An example of a suitable particle counter 50 suitable for use system 10 is manufactured by Particle Measuring Systems (PMS), Inc. of Boulder, Colo. The PMS, Inc. model Micro LPC-HS can detect particles having an equivalent optical scattering diameter as small as 50 nm, with a counting efficiency of >80% at 80 nm using a 633 nm HeNe laser. The instrument requires a sample flow rate of 0.1 standard cubic feet per minute (SCFM) or 2.8 standard liters per minute (SLPM). The Micro LPC-HS has a zero count level of <2/ft$^3$, or <0.2/minute, and can measure particle concentrations up to 80,000/ft$^3$. The instrument has 8 size channels, with thresholds at 50, 100, 150, 200, 300, 500, 700 and 1,000 nanometers (nm). The sampling interval can be set in the range of from 1 second to 100 hours.

In certain preferred embodiments, the particle counter 50 is an optical particle counter (OPC) that allows for automatic real-time particle counting and permits immediate, real-time identification of spurious counts generated by, for example, reaction of silane with residual moisture and oxygen. These reactions can result from inadequate purging/drying of the sampling system during start-up of the sampling process. Such burst states can then be rejected after the steady state particle level of the system is reached, by using the real time counting capability of the OPC.

When not in use, particle counter 50 can be isolated from the system by closing valves V1 and V2. This permits particle counter 50 to remain free of contaminants that may otherwise enter the system.

In preferred embodiments of the present invention, particle counter 50 is combined with capture filter 60 to provide a means of determining when such spurious counts are removed from the system. In such embodiments of the present invention, a gas feed stream can be simultaneously or sequentially directed to particle counter 50 and capture filter 60 for measurement. For example, gas feed stream 25 can be first directed to particle counter 50 and then a portion of gas feed stream 25 can be directed to capture filter 60 to corroborate the results observed by particle counter 50 and to further characterize the particles as explained in more detail below. In these embodiments, only then is the isolated capture filter exposed to the incoming gas feed stream 25.

Particle capture filter 60 is preferably located in a parallel leg of the sampling system relative to particle counter 50. Particle capture filter 60 can operate with or without pressure reduction; and the gas feed stream 25 can flow through particle capture filter 60 at full system or reduced pressures. This direct sampling method minimizes the potential for spurious particle counts resulting from "shedding" of pressure reducers and impurities nucleation. Capture filter 60 also permits examination of the captured contaminant particles under various analytical tools such as, but not limited to, scanning electron microscopy (SEM), energy dispersive X-ray spectrometry (EDS), light microscopy, and other means. This technique provides additional information on particle morphology and composition. Such information aids in identification and elimination of particle sources within the system.

In preferred embodiments of the present invention, capture filter 60 has two fittings 71, 72 that allow capture filter 60 to be removed from the system. Capture filter 60 can be readily removed at fittings 71, 72 when valves V3, V4, V17 and V18 are closed.

Once removed from system 10, the particles collected on capture filter 60 can be analyzed by employing the following method. First, the background contamination (i.e., contamination that may be present on the surface of capture filter 60 before exposure to gas feed stream 25) on the surface of capture filter 60 is preferably separated from the sample contamination. Background contamination typically originates during the filter manufacturing and handling process. In this regard, the surface density of background contamination on filter 60 must be measured and accounted for in the particle capture method. Microscopy is used to determine the number of background particles on an un-exposed filter. This can be done by examining only a part of the filter surface. A portion of the filter's surface area, $A_B$, is inspected to obtain the number of background particles, $N_B$, in that area. After exposure to the sample gas or supercritical fluid a portion of the surface area, $A_P$, is inspected to determine the total number of background and captured particles, $N_P$, in that area. The total number of captured particles, N, on the entire surface of the exposed filter is then given as:

$$N=A(N_P/A_P-N_B/A_B),$$

where A is the total surface area of the filter. If V is the volume of sample gas or supercritical fluid passed through the exposed filter, then the concentration of particles per unit volume of sample, C, is given as:

$$C=N/V.$$

Sampling system 10 also has a bypass line 40 to permit cycle/purging of both sides of the particle filter 60, and to permit flow initialization around the filter 60. Bypass line 40 includes valve V5 that, when open, allows for cycle-purging of sampling system 10 with inert gas from inert gas source 30 by a downstream vacuum pump 70, such as, for example, a turbo-molecular vacuum pump. Vacuum pump 70 is in fluid communication with system 10, once valve V6 is open, through flow line 130.

In some embodiments of the present invention, vacuum pump 70 is used to draw sample fluids from low pressure sources. The sample fluid passes through the particle counter 50 or capture filter 60 before passing through vacuum pump 70 and then into emission control system 80. Emission control system 80 and one or more burners 90 may comprise, for example, a gas reclamation system, a combustion system, a vent system, a scrubber system, an adsorption system, an absorption system, or a purification and storage system. Such systems are well known in the art of vent stream emission control.

In certain embodiments of the present invention, capture filter 60 may be a track etch filter or a porous alumina filter. Unlike OPCs, capture filters have no upper limit on measurable particle concentration. Polycarbonate track etch filter membranes are available with pore sizes as small as 15 nm. Alumina filter membranes are available with pore sizes as small as 20 nm. The higher pore density of alumina filters provides a minimal flow resistance at high flow rate. A high flow rate is beneficial in sampling a large volume of gas in a minimum time. The particle capture filter 60 may be housed within a pressure resistant filter housing such as, for example, a Model No. xx4502500 25 mm stainless steel filter housing manufactured by Millipore Corporation of Bedford, Mass. The filter housing contains the filter membrane, which may be sealed therein with a variety of elastomeric materials, such as for example a Teflon™ o-ring. This filter membrane may be used, for example, to capture particles in various high-pressure gases, including silane. The particles within the gas feed stream can be analyzed using a variety of techniques, such as, but not limited to, light microscopy, SEM and EDS, after being captured on the filter.

In preferred embodiments of the present invention, particle capture filter 60 may be a chemically resistant filter media, such as, for example, TEFLON™ microporous membranes. Such membranes are not suitable for EDS or microscopic particle examination due to their rough surface structure. However, particles captured on such filters can be analyzed for composition and total captured mass by digestion or dissolution in various acids or solvents. The acid or solvent is then analyzed through various well known means, including liquid chromatography.

Sampling system 10 is designed for turnkey operation, and connection to any selected gas feed source. The system can be used for periodic cylinder qualification tests, point-by-point particle survey studies of silane distribution systems, or continuous alarmed monitoring of a gas transfill system or a gas distribution system.

The pressure of incoming gas feed stream 25 in system 10 is typically measured by employing a pressure gauge, such as for example a diaphragm-type pressure gauge. In the system depicted in FIG. 2, the sample feed gas is sent to an on-site burner system or 90. However, depending upon the identity of the feed gas stream 25, the sample feed gas may alternatively be vented, reclaimed, or sent to emission control system 80 or adsorber, absorber, scrubber, purifier and storage system (not shown), or recycled back into the main gas feed supply (not shown).

Flow control device 120 is typically employed to control and monitor the rate of sample gas flow through the particle counter or the particle capture filter during testing. Flow control device 120 may include a manually operated flow control valve and a flow meter such as, for example, a mass flow meter, or flow control device 120 may include an automated actuated flow control device such as, for example, a mass flow controller. Sample gas downstream from flow control device 120 can be evacuated through flow line 140, which is also in fluid communication with vacuum pump 70.

In preferred embodiments of the present invention, pneumatically actuated valves can isolate the clean internals of the system when it is not in use. The cycle-purging and sampling sequence can be performed automatically using a process logic controller (PLC) (not shown) before each sample run. The PLC receives input from a pressure transmitter and heat tracing temperature controller to ensure the vacuum-pressure cycle is within specified limits during operation. In certain embodiments, the heat traced lines are held at 100° C. during cycle purging. The system is evacuated to <50 Torr and returned to atmospheric pressure at least 150 times during cycle-purging.

The system is flushed with purified inert gas prior to cycle-purging to eliminate atmospheric gases, and after sampling to remove any residual gas. Depending upon the identity of the gas being sampled, the flush cycle may send these gases to a reclamation system, a burner, or scrubber vessels, such as, for example, when the sample gas comprises silane. In other embodiments, the flush cycle may vent the gas to atmosphere. The purge operation is performed while the system is connected to the gas feed source, before and after the sampling procedure. The sample source valve is closed during the inert gas flush operation. In embodiments where the gas being sampled comprises silane, this purge gas is sent to a silane burner, reclaim system, or scrubber. The inert flush process may also be used to purge-out the silane source connection fitting while the system is disconnected from the silane source. This purge is intended to prevent contaminants from entering the open sampling system. The inert gas will vent out the silane inlet line to atmosphere.

In preferred embodiments of the present invention, such as that depicted in FIG. 2, heat tracing should be included to minimize trace moisture in the system. In these embodiments, all system components upstream of the particle counter and capture filter are preferably heat traced (see bold lines in FIG. 2). Heating tracing comprises electrical resistance heating elements that may be affixed, for example, to the outer surfaces of system tubing, valves, filter housings, pressure regulators, and other components. The heat tracing includes a temperature sensing device, such as, for example, a thermocouple to provide temperature feedback to a temperature indicator, and to a temperature control device such as, for example, a process controller or thermostat. The temperature control device contains circuitry designed to regulate the power to the heating elements such that a set temperature is maintained within the system. Such heating provides ready elimination of trace absorbed moisture from the internal surfaces of the system, and permits removal of trace residual sample fluids from the system following the testing process. In certain embodiments, system 10 may employ a moisture analyzer 100 that can detect residual moisture in the line and may, for example, activate various valves if the level of moisture within the gas feed stream is outside desired levels. In this or other embodiments, system 10 may employ an oxygen sensor that acts in a similar fashion as the moisture analyzer in detecting the presence of oxygen within the gas feed stream.

In another preferred embodiment of the present invention, the method and system described herein may be used to remove trace impurities through the use of one or more purifying devices from a gas feed stream at a higher pressure to provide a purified gas feed stream and to reduce the pressure of the purified gas feed stream to a lower pressure gas feed stream without consequent particle formation. The term "lower pressure gas feed stream" as used herein describes a purified gas feed stream that has been passed through a pressure reducing device, such as without limitation, an automatic pressure regulator, valve, flow restricting orifice, or the like. The pressure of the initial gas feed stream is reduced to a level compatible with the available instrumentation for particle measurement after purification. For example, in one embodiment of the present invention, the gas feed stream may be at an initial pressure ranging from 150 to 10,000 psig. A pressure reducing device then reduces the pressure of a purified gas feed stream to a pressure ranging from 0 to 150 psig. The pressure ranges described herein may vary depending upon the initial pressure of the gas feed stream, the type of pressure reducing device used, the particle measurement device, and/or other variables.

The term "purified gas feed stream" as used herein describes a gas feed stream that has been passed through one or more purifying devices to remove various impurities contained therein. The system and method described does not adversely affect such as increase the particle content of the gas feed stream that may be attributable to pressure reducing devices. In certain embodiments, the particle content of the purified gas feed stream is substantially the same as the particle content of the gas feed stream prior to passing through the purifying device.

The term "impurities" as herein refer to small quantities of contaminating substances, such as without limitation siloxanes, hydrocarbons, moisture, and other contaminants depending upon the composition of the gas feed stream, that are present in the initial gas feed stream. In certain embodiments, the impurities present in the gas feed stream would be siloxanes in a silane gas feed stream or hydrocarbons in a nitrogen and/or silane gas feed stream. A purifying device as used herein is a device that removes substantially all of the impurities contained within the gas feed stream (e.g., about 5% by volume and below, or 1% by volume and below, or 0.01% by volume and below) without adversely affecting the chemical composition of the gas. In certain embodiments, the purifying device does not substantially affect the particle content of the gas, or does not substantially remove or add the particles to the purified gas feed stream. In these embodiments, the particle content of the purified gas feed stream is substantially the same as the particle content (i.e., within 10% of the amount of or within 5% of the amount of or within 1% of the amount of particles) of the initial gas feed stream. The purified gas feed stream is then passed through a pressure reducing device to provide a lower pressure gas feed stream. The lower pressure gas feed stream is then sent to a particle counter.

Figure 3:
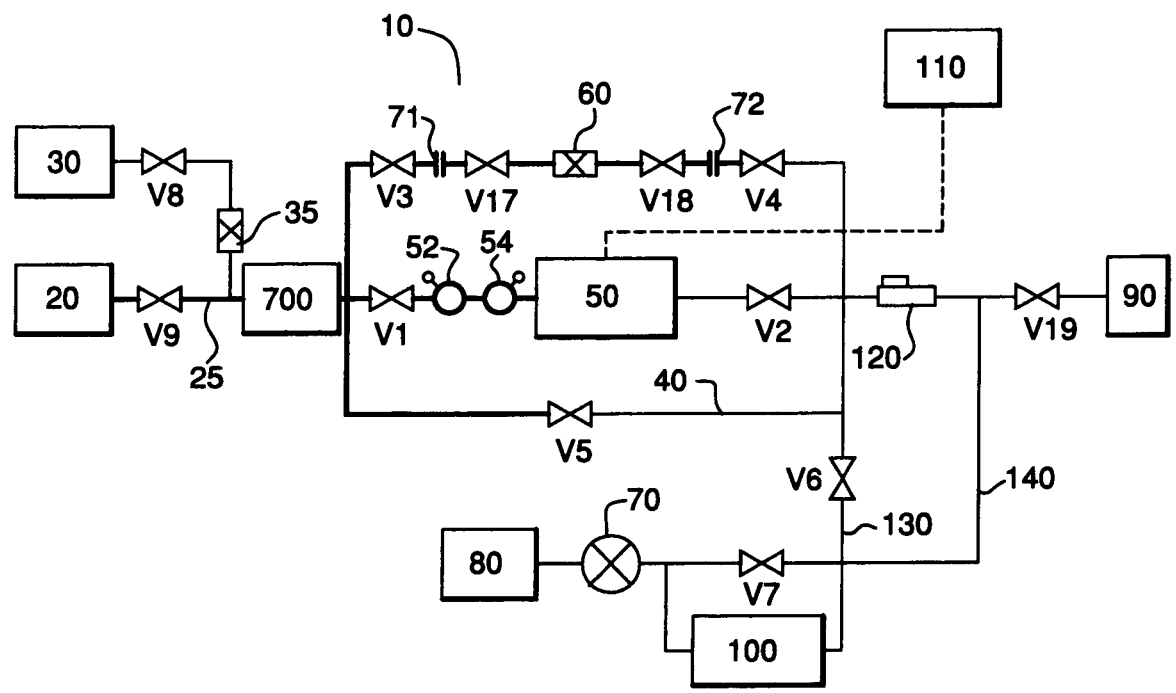
FIG. 3 is a schematic representation of system in accordance with another embodiment of the present invention described herein as an off-line sample system.

Referring now to FIG. 3, another preferred embodiment of the system of the present invention is illustrated. The system of FIG. 3 is similar to the system of FIG. 2 (wherein like numbers refer to like elements) except that the system of FIG. 3 comprises a purifying device 700 to remove impurities such as, for example, molecular impurities within gas feed stream 25. Purifying device 700 used with the system and method described herein may be, for example, a diffusion denuder, a cold trap, or both. Diffusion denuders have not been used in the prior art as a means to purify specialty process gases operated at elevated pressures, combined with downstream pressure reduction devices, and/or used to prevent nucleation of trace molecular impurities during the process of gas expansion. Likewise, while cold trapping is well known in the art of gas technology as a means to remove impurities from flowing streams, cold trapping has typically not been applied as a means to remove impurities from pressurized streams prior to pressure reduction nor as a means to prevent formation of particles during pressure reduction.

Figure 4A:
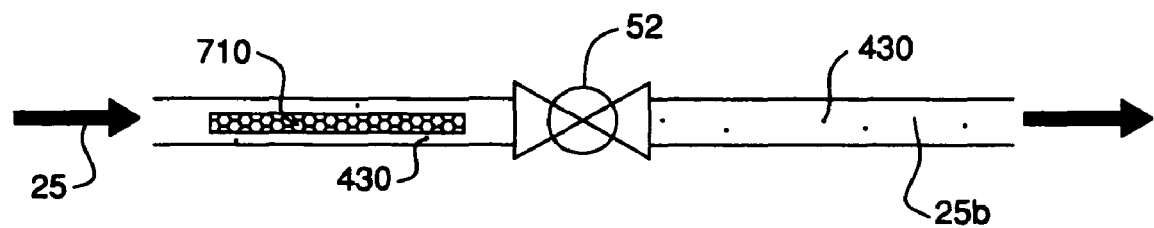
FIGS. 4A-C are illustrations of several embodiments of an aspect of the present invention.
Figure 4B:
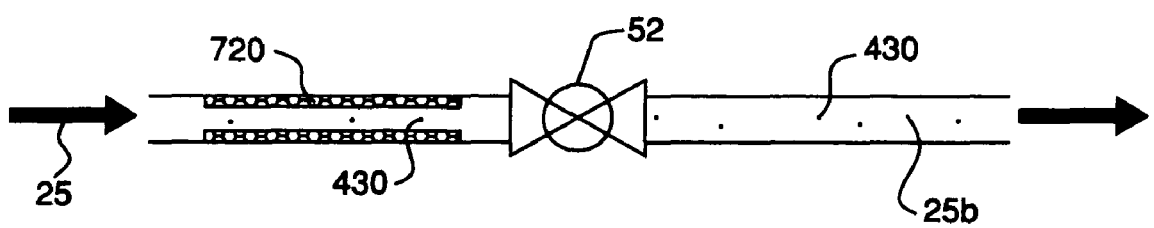
Figure 4C:
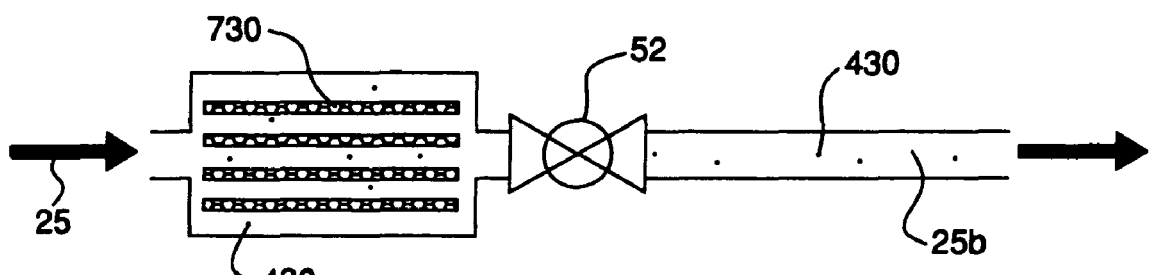

In one preferred embodiment of the present invention, purifying device 700 is a diffusion-type denuder device such as, for example, a central denuder 710, annular denuder 720, and fin denuder 730 placed upstream of a pressure reducing device 52 depicted in FIGS. 4A, 4B, and 4C, respectively. The lower pressure gas feed stream 25*b* may then be used, in certain embodiments, to provide a sample stream for low-pressure particle counting instrument 50 in FIGS. 2 and 3.

Diffusion-type denuder devices, herein referred to as "diffusion denuders", are well known in the art of impurities and particle detection. Such devices are typically used in atmospheric sampling or other applications requiring removal of molecular impurities without a change to the air-borne particle content. They are also used as a means to collect trace molecular impurities from air samples onto surfaces for later analysis. Such devices are typically designed for use under conditions of atmospheric pressure and temperature, and have been shown to remove more than 99% of air-borne impurities. Diffusion denuders are tubular flow devices that utilize the comparatively high diffusion rates of molecular impurities to remove them from a gas feed stream, without significantly affecting the suspended particle content. Typical particles have a much lower rate of diffusion in a gas feed stream than do typical molecules. This is primarily due to the substantially greater sizes of particles than molecules. For example, 0.02 micrometer particles have a diffusion coefficient in $N_2$ of only 0.019 cm$^2$/s. (Larger particles have even smaller diffusion coefficients due to their lower mobilities in a gas.) In contrast, typical diffusion coefficients for molecular impurities are greater in value. For example, water has a diffusion coefficient in air of 0.22 cm$^2$/s. Therefore, suspended particles tend to follow the flowing gas, while molecular impurities tend to diffuse more readily to surfaces.

In a preferred embodiment of the present invention, the purifying device 700 is a diffusion denuder that removes substantially all of the molecular impurities from the gas feed stream without significant removal of particulates contained therein. Variables that are used to effect the removal rate of the particles within the gas feed stream prior to pressure reduction include the flow rate of the gas, the denuder length, and the hydraulic radius of the device. In a diffusion denuder, the impurities within the gas feed stream are exposed to a chemically reactive surface, an absorbent or other purifying medium contained behind a screen-type or porous barrier. The barrier is designed to physically contain a granular or pelletized purifying medium, and to prevent direct gas flow through the medium bed. Thus, the impurities remain in the purifying medium whereas the balance of the gas feed stream passes through as a purified feed gas. In one particular example of a diffusion denuder that is used to remove moisture impurities from air, the purifying medium within the diffusion denuder consists of a drying material, such as Drierite™ which surrounds a gas feed stream containing air and is separated from the air by a tubular stainless steel screen. Moisture diffuses from the air through the screen to the surrounding Drierite™ and is removed. In yet another example of a conventional denuder to remove ammonia impurities from a gas feed stream containing air, the purifying device is a glass flow tube that is internally coated with oxalic acid to absorb the $NH_3$ impurities from the gas feed stream without affecting its particle content.

In preferred embodiments of the present invention, the purifying medium within the purifying device such as a denuder may consist of various well known adsorbent, absorbent or catalytic materials, such as activated carbon, desiccants (e.g., Drierite™), phenolic resins (e.g., Ambersorb™), nickel catalyst, copper catalyst, etc., which are selected depending upon the type of impurities to be removed and/or the gas feed stream composition. In one example of system described herein, a purifying medium consisting of Ambersorb™ pellets is contained in a packet consisting of a stainless steel screen tube which is closed at both ends, and around which the gas feed stream flows. For example, in the embodiment shown in FIG. 4A (wherein like numbers refer to like elements relative to FIGS. 2 and 3), a gas feed stream 25, such as one comprising $SiH_4$ at a pressure of 1400 psig, containing particles 430 is passed through a central denuder 710 prior to passing through pressure reducer 52, for example. In this particular embodiment, central denuder 710 may remove, for example, impurities such as siloxanes and trace hydrocarbons from the initial $SiH_4$ gas feed stream while allowing the actual particles, originating in the pressurized storage vessel (not shown) to pass unimpeded. Central denuder 710 may comprise, for example, a ¼-inch diameter tubular screen or, alternatively several such tubular screens arranged longitudinally in series within a ½-inch diameter pressurized gas tube. The pressure of the $SiH_4$ gas feed stream can be reduced to a lower pressure gas feed stream 25b, such as for example, 80 psig, using a high purity automatic pressure regulator (not shown). The lower pressure gas feed stream of $SiH_4$ 25b containing particles 430 may then flow to a conventional low pressure particle counting instrument (not shown).

In another preferred embodiment of the present invention, a purifying medium consisting of granular activated carbon such as, for example, annular denuder 720, comprises a barrier consisting of a tubular stainless steel screen through which the initial gas feed stream flows. For example, in one particular embodiment, an initial gas feed stream 25 comprising nitrogen at a pressure of 2000 psig may be passed through annular denuder 720 prior to passing through pressure reducer 52 as shown in FIG. 4B. In this embodiment, annular denuder 720 removes problematic impurities such as moisture and trace hydrocarbons from the initial $N_2$ gas feed stream while allowing the actual particles originating in the pressurized storage vessel 20 to pass unimpeded. In one particular embodiment, annular denuder 720 may comprise a ¼-inch diameter tubular screen or, alternatively several such tubular screens, arranged longitudinally in series within a ½-inch diameter pressurized gas tube. The pressure of the purified $N_2$ gas feed stream may then be reduced to 0 psig using pressure reducing device 52 such as, for example, a flow restricting orifice. The lower pressure gas feed stream 25b containing particles 430 may then flow to a conventional low pressure particle counting instrument (not shown).

Other similar geometries comprising a purifying medium contained behind a porous barrier and located upstream of a suitable pressure reducing device can be used with the system and method described herein. Such geometries may, for example, consist of flat packets composed of purifying medium contained in a screen-type or porous barrier, and inserted into a gas line upstream of a pressure reducer.

In yet another embodiment, the purifying device comprises granular or pelletized purifying medium affixed to an exposed surface inside the pressurized gas lines in order to provide a means for exposure to the gas feed stream 25 such as the annular denuder 720 depicted in FIG. 4B. The medium is affixed using a suitable adhesive material. In this embodiment, no barrier is required to separate the medium from the gas feed stream. An example of yet another embodiment is shown in FIG. 4C wherein the purifying device is a fin denuder 730 wherein the purifying medium is affixed to the internal wall of the gas line or, alternatively other internal surfaces, such as flat fins, shutters, vessels, and the like, to provide a large surface area for impurities removal, while not impeding the transport of gas-borne particles 430 contained therein or prior to pressure reduction to ensure accurate particle measurement.

In certain embodiments, the system and method described herein may allow for replacement or regeneration of the purifying medium. Regeneration may be accomplished using methods well known in the art of gas purification, such as, but not limited to, exposure to high purity inert regeneration gas at elevated temperatures. Replacement is accomplished by removal of the denuder material, or of an entire central denuder device from the gas line.

In yet another embodiment, the purifying device may comprise cryogenic cold trapping of higher condensation point/freezing point impurities to remove impurities prior to pressure reduction without affecting the particle content in the stream.

Referring to FIGS. 2 and 3, system 10 may employ a computer 110 that is in electrical communication with, for example, particle counter 50, the PLC, or other system components. Computer 110 can operate certain valves within the system to automate the system based upon certain parameters within the gas feed stream (i.e., particle concentration, pressure, temperature, moisture content, oxygen content, etc.). In preferred embodiments, system 10 may also employ a sensor (not shown) that measures the amount of particulate within the gas feed stream and a controller (not shown) that is electrical communication with the sensor such that if the sensor measures the amount of particulate at a point that is above a set point, then the sensor directs the sample stream inlet valve to close.

A preferred method for measuring particle content within a gas feed stream according to the present invention comprises the steps of passing at least a portion of a gas feed stream through a purifying device to provide a purified gas feed stream wherein the purifying device does not substantially remove the particles contained within the purified gas feed stream, wherein the gas feed stream is at a first pressure. Next, for example, a portion of the purified gas feed stream can be directed to a pressure reducing device to reduce the pressure of the portion of purified gas feed stream to a pressure that is lower than the first pressure. Next, the particle content contained within the purified gas feed stream is measured by passing the portion of purified gas feed stream that is at a pressure lower than the first pressure to a particle counter and by passing another portion of the purified gas feed stream to a particle capture filter, wherein the particle capture filter is arranged in parallel with the particle counter.

Additional objects, advantages, and novel features of this invention will become apparent to those skilled in the art upon examination of the following examples thereof, which are not intended to be limiting.

EXAMPLES

Example 1

A particle counting system of the type shown in FIGS. 2 and 3 was connected to various compressed gas cylinders. A pressure and corrosion resistant particle counter [Particle Measuring Systems (PMS), Inc. model Cylinder Gas System (CGS) M100] was used in the system. Therefore, no reduction in sample pressure was required upstream of the instrument. This instrument measures particles as small as 0.16 micrometer in size suspended in gas sample streams. Sample gas was withdrawn from each cylinder at a flow rate of 19 actual $cm^3$/min. and passed through the instrument. No particle capture filter was used in these tests. No filtration of the sample gas was made upstream of the instrument. Heat tracing of the sample lines, typically to 50° C., was used to minimize droplet formation in condensable gases, and to maintain a low moisture content in the sample line tubing. Sample gas pressure reduction, flow control, abatement and venting were provided downstream of the instrument. The sampling system was pressure cycled and heated to remove atmospheric contaminants prior to sampling. After pressure cycling at least 57 standard liters (2 standard $ft^3$) of gas were sampled from each test cylinder. Test results are shown in Table 1.

The low particle concentration in each case demonstrates there are no interferences in the measurement from external contamination, droplet formation or other sources of inaccuracy using this invention.

TABLE 1

| | Measured Concentration of Particles ≧0.16 Micrometer in Pressurized Gas Cylinders | |
|---|---|---|
| Gas | Cylinder Pressure (psig) | Particles/ standard liter |
| $CHF_3$ | 580 | 0 |
| $C_2F_6$ | 590 | 0 |
| He | 2640 | 0 |
| $H_2$ | 2525 | 0 |
| HCl | 632 | 0.18 |
| $N_2$ | 2100 | 0 |
| $N_2O$ | 400 | 0.13 |
| $SF_6$ | 274 | 13 |
| $CF_4$ | 1770 | 3.7 |
| Ar | 2655 | 0.25 |
| $Cl_2$ | 96 | 0.33 |
| $NF_3$ | 1450 | 0.044 |
| $NH_3$ | 135 | 0.030 |
| $O_2$ | 2651 | 2.2 |
| $SiH_4$ | 766 | 0.047 |

Example 2

A particle counting system of the type described in this patent application was connected to a compressed $SiH_4$ (silane) gas cylinder. No filtration of the sample gas was made upstream of the instrument or particle capture filter. Heat tracing of the sample lines, typically to 50° C., was used to maintain a low moisture content in the sample line tubing. Sample gas flow control and abatement were provided downstream of the particle counter and particle capture filter. The sampling system was pressure cycled and heated to remove atmospheric contaminants prior to sampling.

A pressure resistant particle counter [Particle Measuring Systems (PMS), Inc. model Cylinder Gas System (CGS) M100, Particle Measuring Systems, Inc., Boulder, Colo.] was used in the system. Therefore, no reduction in sample pressure was required upstream of the instrument. This instrument measures particles as small as 0.16 micrometer in size suspended in gas sample streams. Sample gas was withdrawn from the 776 psig $SiH_4$ cylinder at a flow rate of 19 actual $cm^3$/min. and passed through the instrument. A particle concentration of only 0.047 per standard liter was measured in the gas. This low particle concentration demonstrates there are no interferences in the test system from external contamination, particle formation or other sources of inaccuracy using this invention.

A pressure and corrosion resistant particle capture filter assembly was also used in the test system. The capture filter consisted of a 3.8 cm diameter Whatman polycarbonate track etch membrane having 0.1 micrometer pores. The sample $SiH_4$ flowed at approximately 1 standard liter per minute from the cylinder. Sampling proceeded for approximately 362 minutes. Therefore a total sample volume of approximately 362 standard liters of $SiH_4$ was therefore passed through the particle capture filter.

Figure 5:
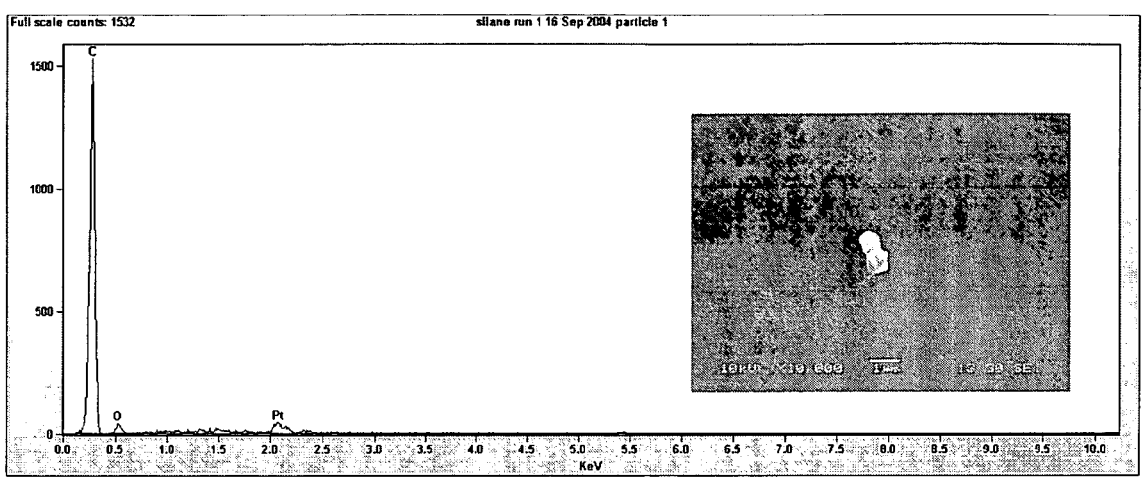
FIG. 5 is an SEM micrograph and an EDS spectrum of a particle captured by the system of the present invention.

The particle capture filter was then examined under field emission SEM (FESEM) at 50,000× magnification. The SEM examination was performed by manually advancing the inspection point in a raster pattern across the filter. A total of 901 locations were examined on the filter surface. The total inspected area represented approximately 0.0015% of the exposed filter surface. Energy Dispersive X-Ray Spectroscopy (EDS) was used to determine the compositions of four of the observed surface particles. A SEM micrograph and EDS spectrum of one of the surface particles is shown in FIG. 5. The data indicate that the surface particles were caused by platinum metal coating of the capture filter prior to SEM and EDS examination. No other particle types were found in the examination.

These tests show that the compositions of particles on surfaces exposed to reactive sample gases can be obtained, and the sources of the particles can be determined using this invention. The EDS data also reinforces the particle counter observations indicating little innate particle content in the $SiH_4$ sample stream.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:

1. A system for measuring and/or analyzing particles within a gas feed stream, the system comprising:
   a purifying device to provide a purified gas feed stream wherein the purifying device removes substantially all of the molecular impurities in the purified gas feed stream but does not remove the particles contained within the purified gas feed stream;
   a particle counter in fluid communication with the purifying device; and
   a particle capture filter in fluid communication with the purifying device, wherein the particle capture filter comprises a removable membrane and said particle capture filter is arranged in parallel with the particle counter and wherein the gas feed stream passes through the purifying device to provide the purified gas feed stream prior to entering the particle counter and/or the particle capture filter.

2. The system of claim 1 wherein the purifying device comprises a diffusion denuder, a cold trap, or both.

3. The system of claim 1 further comprising a microprocessor that is in electrical communication with at least the particle counter.

4. The system of claim 1 further comprising:
   a sample stream inlet valve located upstream of the particle counter
   a sensor that measures the amount of particulate within the gas feed stream upstream of the sample stream inlet valve; and
   a controller that is electrical communication with the sensor such that if the sensor measures the amount of particulate at a point that is above a set point then the controller directs the sample stream inlet valve to close prior to the purified gas feed stream entering the particle counter.

5. A system for measuring particle content within a lower pressure gas feed stream, the system comprising:
   a purifying device to remove impurities within a gas feed stream and provide a purified gas feed stream having a first pressure wherein the purifying device removes substantially all of the molecular impurities in the purified gas feed stream but does not remove the particles contained within the purified gas feed stream;
   a pressure reducing device in fluid communication with the purifying device wherein the purified gas feed stream is passed through the pressure reducing device to provide a lower pressure gas feed stream having a pressure that is lower than the first pressure;
   a particle counter that measures the particle content within the lower pressure gas feed stream; and
   a particle capture filter, wherein the particle capture filter comprises a removable membrane and said particle capture filter is arranged in parallel with the particle counter.

6. The system of claim 5 wherein the purifying device comprises a diffusion denuder, a cold trap, or both.

7. The system of claim 5 further comprising a microprocessor that is in electrical communication with at least the particle counter.

8. The system of claim 5 further comprising a vacuum pump wherein the vacuum pump is downstream of the particle counter and/or the particle capture filter.

9. The system of claim 5 further comprising a sample line heat tracing system upstream of the particle counter and/or particle capture filter comprising a temperature sensor, a heating source, and a controller that is in electrical communication with the temperature sensor and the heating source.

10. The system of claim 5 further comprising a moisture analyzer upstream of the particle counter and/or particle capture filter.

11. The system of claim 5 further comprising an emission control device wherein the emission control device is downstream of the particle counter and/or the particle capture filter.

12. The system of claim 5 further comprising at least one inert gas inlet system wherein the at least one inert gas inlet system is upstream of the particle counter and/or the particle capture filter.

13. The system of claim 5 further comprising:
   a sample stream inlet valve located upstream of the particle counter
   a sensor that measures the amount of particulate within the gas feed stream upstream of the sample stream inlet valve; and
   a controller that is electrical communication with the sensor such that if the sensor measures the amount of particulate at a point that is above a set point then the controller directs the sample stream inlet valve to close prior to the purified gas feed stream entering the particle counter.

14. A system for measuring and/or analyzing particles within a gas feed stream, the system comprising:
   a purifying device to provide a purified gas feed stream wherein the purifying device removes substantially all of the molecular impurities in the purified gas feed stream but does not remove the particles contained within the purified gas feed stream;
   a particle counter in fluid communication with the purifying device;
   a particle capture filter in fluid communication with the purifying device wherein the particle capture filter is arranged in parallel with the particle counter;
   a microprocessor that is in electrical communication with at least the particle counter;
   a vacuum pump;
   a moisture analyzer;

an emission control device;

at least one inert gas inlet system; and a sample line heat tracing system comprising a temperature sensor, a heating source, and a controller that is in electrical communication with the temperature sensor and the heating source wherein the at least one inert gas inlet system, the sample line heat tracing system, and the moisture analyzer are upstream of the particle counter and/or the particle capture filter; and wherein the vacuum pump and the emission control device are downstream of the particle counter and/or the particle capture filter.

15. The system of claim 14 further comprising:

a sample stream inlet valve located upstream of the particle counter a sensor that measures the amount of particulate within the gas feed stream upstream of the sample stream inlet valve; and a controller that is electrical communication with the sensor wherein if the sensor measures the amount of particulate at a point that is above a set point then the controller directs the sample stream inlet valve to close prior to the purified gas feed stream entering the particle counter.

16. The system of claim 14 wherein the purifying device comprises a diffusion denuder, a cold trap, or both.

17. A method for measuring particle content within a gas feed stream, the method comprising:

passing at least a portion of a gas feed stream through a purifying device to provide a purified gas feed stream wherein the purifying device removes substantially all of the molecular impurities in the purified gas feed stream but does not substantially remove the particles contained within the purified gas feed stream, wherein the gas feed stream is at a first pressure;

directing portion of the purified gas feed stream to a pressure reducing device to reduce the pressure of the portion of purified gas feed stream to a pressure that is lower than the first pressure; and measuring the particle content contained within the purified gas feed stream by passing the portion of purified gas feed stream that is at a pressure lower than the first pressure to a particle counter and by passing another portion of the purified gas feed stream to a particle capture filter wherein the another portion of the purified gas feed stream passed through the particle capture filter is at the first pressure or at the pressure lower than the first pressure and wherein the particle capture filter is arranged in parallel with the particle counter.

18. The method of claim 17 wherein the measuring step comprises simultaneously passing the portion of purified gas feed stream that is at a pressure lower than the first pressure to a particle counter and the another portion of the purified gas feed stream to a particle capture filter.

19. The method of claim 17 wherein the purifying device comprises a diffusion denuder, a cold trap, or both.

20. A method for analyzing particle content within a gas feed stream with an apparatus that comprises a purifying device to provide a purified gas feed stream, a particle counter; a microprocessor that is in electrical communication with at least the particle counter; and a particle capture filter comprising a removable membrane and wherein the particle capture filter is arranged in parallel with the particle counter, the method comprising:

providing a gas within the gas feed stream;

measuring a particle content contained within the purified gas feed stream by passing a portion of the purified gas feed stream to the particle counter;

passing another portion of the purified gas feed stream to the particle capture filter to capture particles in the purified gas feed stream; and analyzing the captured particles by microscopy.

21. The method of claim 20 wherein the measuring step and the passing step occur simultaneously.

22. The method of claim 20 wherein the measuring step and the passing step occur in sequence.

* * * * *

UNITED STATES PATENT AND TRADEMARK OFFICE
CERTIFICATE OF CORRECTION

| | | |
|---|---|---|
| PATENT NO. | : 7,867,779 B2 | Page 1 of 1 |
| APPLICATION NO. | : 11/340641 | |
| DATED | : January 11, 2011 | |
| INVENTOR(S) | : Wayne Thomas McDermott, Richard Carl Ockovic and Dean Van-John Roth | |

It is certified that error appears in the above-identified patent and that said Letters Patent is hereby corrected as shown below:

Column 15, Line 56

In claim 4 insert --;-- after the word counter

Column 16, Line 42

In claim 13 insert --;-- after the word counter

Column 17, Line 16

In claim 15 insert --;-- after the word counter

Column 18, Line 27

In claim 20 insert --passing at least a portion of the gas feed stream to the purifying device to provide a purified gas feed stream, wherein the purifying device removes substantially all of the molecular impurities in the purified gas feed stream but does not substantially remove the particles contained within the purified gas feed stream;--

Column 18, Line 31

In claim 20 delete the word "purified"

Signed and Sealed this

Seventeenth Day of May, 2011

David J. Kappos
*Director of the United States Patent and Trademark Office*